(12) United States Patent
Pauley et al.

(10) Patent No.: US 10,750,984 B2
(45) Date of Patent: Aug. 25, 2020

(54) METHODS AND DEVICES FOR DETECTING INTENSITY OF LIGHT WITH TRANSLUCENT DETECTOR

(71) Applicant: Cercacor Laboratories, Inc., Irvine, CA (US)

(72) Inventors: Kevin Pauley, Lake Forest, CA (US); Cristiano Dalvi, Lake Forest, CA (US); Hung Vo, Fountain Valley, CA (US); Jesse Chen, Foothill Ranch, CA (US); Ferdyan Lesmana, Irvine, CA (US); Jeroen Poeze, Rancho Santa Margarita, CA (US); Sean Merritt, Lake Forest, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 209 days.

(21) Appl. No.: 15/850,755

(22) Filed: Dec. 21, 2017

(65) Prior Publication Data

US 2018/0199871 A1    Jul. 19, 2018

Related U.S. Application Data

(60) Provisional application No. 62/437,996, filed on Dec. 22, 2016.

(51) Int. Cl.
*A61B 5/1455*    (2006.01)
*A61B 5/145*    (2006.01)
(Continued)

(52) U.S. Cl.
CPC ...... *A61B 5/14552* (2013.01); *A61B 5/14532* (2013.01); *A61B 5/14535* (2013.01);
(Continued)

(58) Field of Classification Search
None
See application file for complete search history.

(56) References Cited

U.S. PATENT DOCUMENTS 4,431,429 A    2/1984    Booth
4,443,107 A    4/1984    Alexander et al.
(Continued)

OTHER PUBLICATIONS

International Search Report and Written Opinion, re PCT Application No. PCT/US2017/067909, dated Mar. 15, 2018.

*Primary Examiner* — Eric F Winakur
*Assistant Examiner* — Marjan Fardanesh
(74) *Attorney, Agent, or Firm* — Knobbe, Martens, Olson & Bear, LLP

(57) ABSTRACT

An optical measurement device includes a light source, a first detector, and a second detector. The light source emits light to a measurement site of a patient and one or more detectors detect the light from the light source. At least a portion of a detector is translucent and the light passes through the translucent portion prior to reaching the measurement site. A detector receives the light after attenuation and/or reflection or refraction by the measurement site. A processor determines a light intensity of the light source, a light intensity through a tissue site, or a light intensity of reflected or refracted light based on light detected by the one or more detectors. The processor can estimate a concentration of an analyte at the measurement site or an absorption or reflection at the measurement site.

20 Claims, 6 Drawing Sheets

(51) Int. Cl.
    *G01J 1/16*      (2006.01)
    *G01N 21/47*     (2006.01)
    *G01N 21/31*     (2006.01)
    *G01N 21/49*     (2006.01)
    *A61B 5/00*      (2006.01)
    *G01N 21/59*     (2006.01)

(52) U.S. Cl.
    CPC ...... *A61B 5/14539* (2013.01); *A61B 5/14542* (2013.01); *A61B 5/14546* (2013.01); *A61B 5/4875* (2013.01); *G01J 1/1626* (2013.01); *G01N 21/31* (2013.01); *G01N 21/4738* (2013.01); *G01N 21/49* (2013.01); *G01N 21/59* (2013.01); *A61B 2562/0238* (2013.01); *G01J 2001/1636* (2013.01); *G01J 2001/1652* (2013.01); *G01N 2021/3181* (2013.01)

(56) References Cited

U.S. PATENT DOCUMENTS

| | | |
|---|---|---|
| 4,770,536 A | 9/1988 | Golberstein |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |

(56) References Cited

U.S. PATENT DOCUMENTS

| | | |
|---|---|---|
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |

(56) References Cited

U.S. PATENT DOCUMENTS

| | | |
|---|---|---|
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,668 B1 | 5/2012 | Nabutovsky et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |

(56) References Cited

U.S. PATENT DOCUMENTS

| | | |
|---|---|---|
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |

(56) References Cited

U.S. PATENT DOCUMENTS

| | | |
|---|---|---|
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 2002/0011568 A1 | 1/2002 | Diekmann |
| 2006/0161054 A1 | 7/2006 | Reuss et al. |
| 2007/0282478 A1 | 12/2007 | Al-Ali et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0317940 A1 | 12/2010 | Kuhn et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2011/0237969 A1 | 9/2011 | Eckerbom et al. |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081100 A1 | 3/2014 | Muhsin et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366507 A1 | 12/2015 | Blank |
| 2015/0380875 A1 | 12/2015 | Coverston et al. |
| 2016/0029932 A1 | 2/2016 | Al-Ali |
| 2016/0051205 A1 | 2/2016 | Al-Ali et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0072429 A1 | 3/2016 | Kiani et al. |
| 2016/0081552 A1* | 3/2016 | Wojtczuk ............ A61B 5/0059 600/473 |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |

(56) References Cited

U.S. PATENT DOCUMENTS

| | | |
|---|---|---|
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |

\* cited by examiner

METHODS AND DEVICES FOR DETECTING INTENSITY OF LIGHT WITH TRANSLUCENT DETECTOR

CROSS-REFERENCE TO RELATED APPLICATIONS

The present application claims priority benefit to U.S. Provisional Application No. 62/437,996, entitled "METHODS AND DEVICES FOR DETECTING INTENSITY OF LIGHT WITH TRANSLUCENT DETECTOR," filed Dec. 22, 2016, which is hereby incorporated herein by reference in its entirety.

FIELD OF THE DISCLOSURE

The present disclosure relates to the field of non-invasive optical based sensors that include a translucent detector to detect an intensity of incident light, an intensity of light transmitted through a measurement site, and/or an intensity of light reflected or refracted by a measurement site.

BACKGROUND

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximetry system consists of a sensor attached to a patient, a monitor, and a cable connecting the sensor and monitor. Conventionally, pulse oximetry sensors include a light source(s) characterized by a plurality of wavelengths of known spectra transmitting optical radiation into or reflecting off a measurement site, such as, body tissue carrying pulsing blood and/or interstitial fluid. After attenuation by tissue and fluids of the measurement site, a photodetection device(s) detects the attenuated light and outputs a detector signal(s) responsive to the detected attenuated light. A signal processing device(s) process the detector(s) signal(s) and outputs a measurement indicative of a blood constituent of interest, such as glucose, oxygen saturation, methemoglobin, carboxyhemoglobin, glycated hemoglobin, respiration rate, pulse rate, total hemoglobin, other physiological parameters, or other data or combinations of data useful in determining a state or trend of wellness of a patient.

The sensor is typically attached to a patient's finger or toe, or a very young patient's foot. For a finger, the sensor is configured so that the light source (for example, an LED) projects light through the fingernail and into the blood vessels and capillaries underneath. The photodiode is positioned at the fingertip opposite the fingernail so as to detect the transmitted light as it emerges from the finger tissues.

SUMMARY

The present disclosure provides an improved sensor design which enables more accurate estimates of incident light, as well as a concentration of one or more analytes of interest present at a measurement site. An optical measurement device according to the present disclosure can include a light source, a first detector, and a second detector. The light source can be configured to emit light to a measurement site, and the first detector can be configured to receive incident light from the light source. At least a portion of the first detector can be translucent and the incident light can pass through the translucent portion prior to reaching the measurement site. The second detector can be configured to receive the light after attenuation by the measurement site.

The device of the preceding paragraph may also include any combination of the following features described in this paragraph, among others described herein. The optical measurement device can be a pulse oximetry device. The measurement site can include a tissue site of a patient. The measurement site can include biological material. The measurement site can include non-biological material.

The device of any of the preceding paragraphs may also include any combination of the following features described in this paragraph, among others described herein. The first detector can be proximal to the light source with respect to the measurement site. The first detector can be proximal to the light source with respect to the second detector. The second detector can be distal to the first detector with respect to the measurement site.

The device of any of the preceding paragraphs may also include any combination of the following features described in this paragraph, among others described herein. The light source can include one or more light emitting diodes (LEDs). The one or more LEDs can be superluminescent light emitting diode (SLED). The light emitted by the light source can be optical radiation of red, infrared, near infrared or other wavelengths. The first detector can be configured to detect the incident light in real-time. The device can include a housing configured to house the light source. The device can further include flex circuitry, flexible connections, or flexible cabling configured to electrically connect the first detector to the housing. The second detector can include one or more multi-detectors, such as a set of multi-detectors.

The device of any of the preceding paragraphs may also include any combination of the following features described in this paragraph, among others described herein. The first detector can include an antireflective (AR) coating layer, a photodiode layer, and a wafer layer. The photodiode layer can include an Indium-Gallium-Arsenide (InGaAs) PIN photodiode and/or a silicon PIN photodiode. The photodiode layer can be as thin as 2 nanometers. The wafer layer can include an N-type Indium Phosphide (N—InP) wafer. The wafer layer can be about 11 micrometers thick. The first detector further can include a metalized surface for anode/cathode bond pads. The first detector can absorb less than 5% of the light emitted by the light source. One or more physiological parameters can be determined based at least in part on a detected light intensity of the light source by the first detector and the detected light intensity after absorption by the tissue site by the second detector.

The present disclosure also provides a method of estimating a concentration of an analyte of interest at a measurement site. A monitoring system can attach to, attached near, or be directed at the measurement site. The method can include receiving incident light from a light source at a first detector. At least one portion of the first detector can be translucent and the incident light can be received by and pass through the at least one translucent portion before reaching a measurement site. The method can further include determining an intensity of incident light based at least in part on the incident light received by the first detector. The method can further include receiving attenuated light at a second detector. The attenuated light can be the light which emerges from the measurement site. The method can further include determining intensity of light through the measurement site based at least in part on the attenuated light received by the second detector. The method can further include estimating a concentration of an analyte of interest at the measurement site based at least in part on the intensity of the incident light and the intensity of the attenuated light.

The method of the preceding paragraph may also include any combination of the following features described in this paragraph, among others described herein. The measurement site can include a tissue site of a patient. The measurement site can include biological material. The measurement site can include non-biological material. The method can further include estimating one or more physiological parameters based at least in part on the estimated concentration of the analyte of interest at the measurement site. The method can further include predicting blood glucose concentration.

The present disclosure also provides an optical measurement device that includes a light source configured to emit light to a measurement site, and a detector that includes a translucent portion. The detector can be configured to detect light as it passes through that translucent portion.

The device of the preceding paragraph may also include any combination of the following features described in this paragraph, among others described herein. The optical measurement device can be a pulse oximetry device. The measurement site can include a tissue site of a patient. The measurement site can include biological material. The measurement site can include non-biological material. The detector can be configured to detect incident light of the light source before light from the light source is attenuated by the measurement site. The detector can be configured to detect light reflected or refracted by the measurement site.

The device of any of the preceding two paragraphs may also include any combination of the following features described in this paragraph, among others described herein. The detector can be a first detector and can be configured to detect light before the light is attenuated by the measurement site. The device can further include a second detector configured to receive the light after attenuation by the measurement site. The first detector can be proximal the tissue site with respect to the second detector.

A system, method, or device having any of the features described herein or illustrated in the drawings.

This disclosure describes embodiments of non-invasive methods, devices, and systems for measuring a blood and/or interstitial fluid constituent (which may also be referred to as an analyte), and/or substance such as oxygen, carboxyhemoglobin, methemoglobin, total hemoglobin, glycated hemoglobin, glucose, proteins, lipids, a percentage thereof (for example, saturation), or for measuring many other physiologically relevant patient characteristics. These characteristics can relate, for example, to pulse rate, hydration, trending information, blood oxygen level and analysis, and the like. For example, these measurements can be taken using a non-invasive optical sensor.

This disclosure describes embodiments of non-invasive methods, devices, and systems for detecting intensity of light emitted from a light source of an optical measurement device. The optical measurement device can include a pulse oximeter and/or a spectrophotometer. An optical measurement device or system can determine the power going into a patient's tissue and estimate a concentration of an analyte of interest at the tissue site. In some cases, the optical measurement device or system can estimate absorption of the tissue.

The optical measurement device can be configured to measure tissue of a patient and includes a light source and one or more detectors. The optical measurement device can be attached to the patient measurement site using adhesives, straps, clips, bandages or other attachment devices. The light source can project light through a tissue site of a patient. A detector can detect the light as it emerges from the light source. At least a portion of the detector can be translucent. Light projected from the light source can pass through the translucent portion of the detector prior to reaching the tissue site of the patient. A detector can also detect light as it emerges from the patient's tissue. In addition or alternatively, a detector can also detect light that is reflected or refracted from the patient's tissue. In some cases, these are the same sensor. In some cases, these are different sensors.

The present disclosure also provides that one or more physiological parameters can be determined based at least in part on a detected light intensity of a light source by a first detector and a detected light intensity after absorption by a tissue site by a second detector. The second detector can include a set of detectors.

The present disclosure also provides embodiments for a method of estimating a concentration of an analyte of interest at a tissue site of a patient by a patient monitoring system is provided. The method includes receiving light from a light source at a first detector wherein at least one portion of the first detector is translucent and the light is received by and passes through the at least one translucent portion before reaching a tissue site of a patient; determining a light intensity of the light source based at least in part on the light received by the first detector; receiving attenuated light at a second detector, wherein the attenuated light is the light which emerges from a tissue site of the patient; determining light intensity through a tissue site based at least in part on the attenuated light received by the second detector; and estimating a concentration of an analyte of interest at the tissue based at least in part on the incident light (for example, an light intensity of the light source) detected by the first detector and the light intensity through the tissue site detected by the second detector. The second detector can include a set of detectors.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

DETAILED DESCRIPTION

Figure 1A:
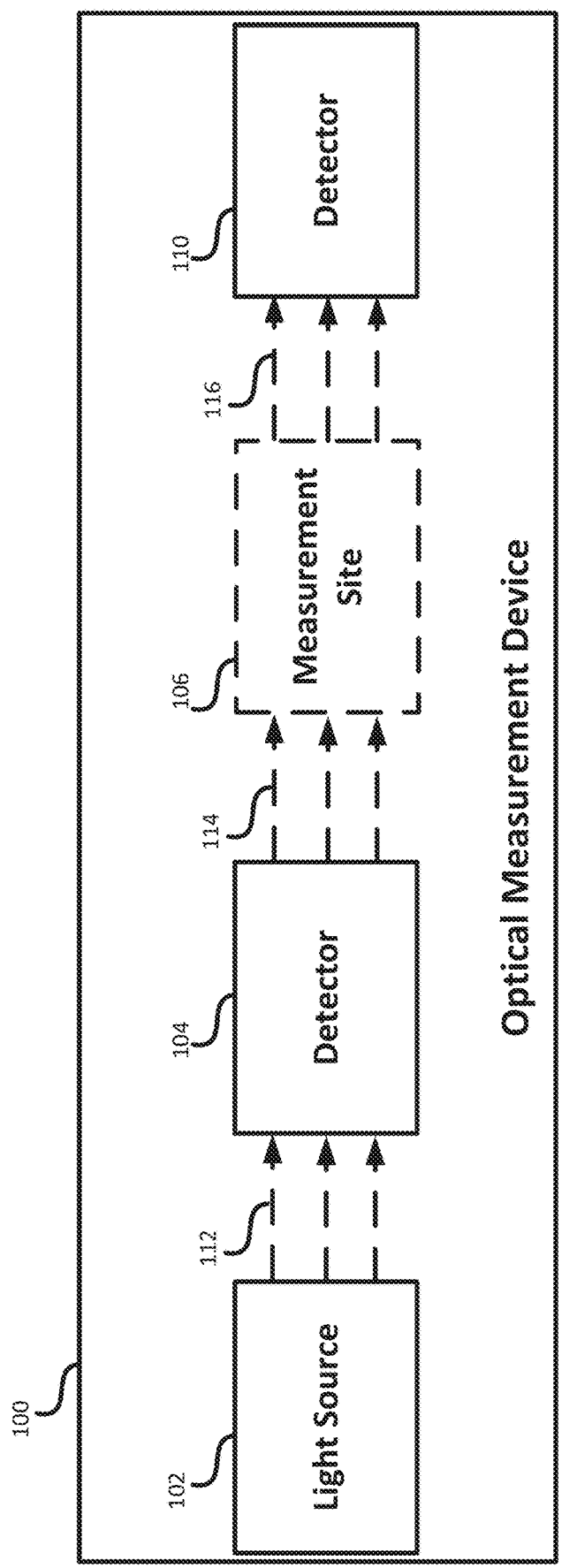
FIGS. 1A and 1B illustrate block diagram of example optical measurement devices.

Beer's Law (also known as the Beer-Lambert Law) relates the attenuation of light to properties of a material. In particular, Beer's law states that absorbance of a material is proportional to the concentrations of the attenuating species in the material sample. The relationship between these parameters can be expressed as:

$$A = \epsilon * b * c \quad (1)$$

where A is the absorbance of the material at a given wavelength of light, ε is the molar absorptivity or extinction coefficient (L mol$^{-1}$ cm$^{-1}$), unique to each molecule and varying with wavelength, b is the length of the light path through the material (cm), and c is the concentration of an analyte of interest (mol L$^{-1}$).

In addition to absorbance, the concentration of an analyte of interest can be determined based on an intensity of the light transmitted through the material (I) and an intensity of incident light ($I_0$). The relationship between these parameters can be expressed as:

$$I = I_0 * e^{-\epsilon * b * c} \quad (2)$$

Accordingly, the concentration c of an analyte of interest can be determined based on a known intensity of light transmitted through the solution I, an intensity of the incident light $I_0$, a pathlength b, and the molar absorptivity ε at a particular wavelength λ.

However, generally, a precise, real-time measurement of intensity of the incident light ($I_0$) is not known. Conventionally, $I_0$ has been measured in a variety of ways which either do not produce accurate measurements or produce measurements with degrading accuracy over time.

For instance, $I_0$ can be measured accurately during manufacturing. However, because the light source will experience real time fluctuations and power degradation over time, using the manufacturing $I_0$ measurement will eventually lead to inaccuracies and miscalculations of physiological parameters such as glucose.

Moreover, $I_0$ can also be determined by sampling a portion of the projected light. However, the sampled portion of light may not accurately represent the entire beam of projected light unless the light is properly mixed. Mixing light properly usually requires an integrating sphere coated with a diffuse reflective material such as a fluoropolymer. Further, accurate light mixing requires a larger diameter sphere which is in opposition to miniaturize a sensor as much as possible.

In other examples, a reference photodiode can be utilized underneath a side of a light source to capture light emitted out the back of a chip. However, this technique does not provide an accurate representation of the light emitted out the front spectrally and it becomes difficult to capture more than one light source on a single reference photodiode if there are multiple light sources in a sensor.

The forgoing difficulties exemplify a need for an improved $I_0$ measuring technique that provides accurate, real-time $I_0$ detection with low quantum efficacy (for example, low light absorption) and takes up limited space. By accurately determining $I_0$, a system can determine various analyte concentrations or changes in concentration in various kinds of biological (for example, living) or non-biological (for example, non-living) material. In some cases, based at least in part on the concentration of an analyte of interest, a system can determine various other predictions or determinations. For example, in pulse oximeter or spectrographic systems, based on the concentration of an analyte of interest, the system can determine or predict physiological parameters, such as glucose or other analyte values. Similar predictions or determinations can be made when the measuring site includes non-biological material.

FIG. 1A illustrates block diagram of an example optical measurement device. The optical measurement device 100 includes a light source 102 configured to emit light towards a measurement site 106, a first detector 104 configured to detect incident light 112 of the light source 102, and a second detector 110 configured to detect light 116 transmitted through the measurement site 106. As illustrated, the first detector 104 is proximal the light source 102 and distal the second detector 110 with respect to the measurement site 106. In addition, the second detector 110 is distal the light source 102 with respect to the first detector 104 and with respect to the measurement site 106. In some cases, the optical measurement device 100 is a pulse oximetry device or a spectrophotometer and the measurement site 106 is a tissue site of a patient. However, the optical measurement device 100 can be any optical measuring device and the measurement site can include any biological or non-biological material.

The light source 102 can include one or more light emitting diodes (LEDs), superluminescent LEDs (SLEDs), lasers, etc. for transmitting optical radiation (for example, light at one or more wavelengths) 112 into or reflecting off the measurement site 106. For ease of reference, the light (for example, the arrows) depicted in FIG. 1A is characterized at multiple stages within the optical measurement device 100. However, in the example illustrated in FIG. 1A, only the light source 102 emits light. The numbered distinctions (112, 114, 116) represent the differing intensities and wavelengths of light from the light source 102 as the light travels from the light source 102 to the second detector 110. For instance, the first set of arrows 112 represents incident light projected from the light source 102 and detected by the first detector 104; the second set of arrows 114 represents light as it emerges from the first detector 104 and reaches the measurement site 106; and the third set of arrows 116 represent light as it emerges from the measurement site 106. Accordingly, each stage of light 112, 114, 116 may have a differing intensity due to, for instance, absorption and/or attenuation.

The first detector 102 is positioned proximal to the light source 102 so as to advantageously detect incident light 112 or an intensity of incident light, $I_0$, as the incident light 112 emerges from the light source 102. This positioning between the light source 102 and first detector 102 allows for a highly accurate real-time $I_0$ detection by the first detector 104 before any significant reduction in intensity of the light projected by the light source 102.

At least a portion of the first detector 104 can be translucent or partially transparent, thereby acting as a window (and a photodiode) from which all light projected from the light source 102 will pass through prior to reaching the measurement site 106. Advantageously, the photodiode (for example, the translucent portion of the first detector 104) receives all (or a substantial portion) of the incident light 112 projected by the light source 102 and can output a signal responsive to the detected light. Thus, unlike the light sampling method mentioned above, the detected light is accurate representation of the light coming from the light source 102. Additionally, the first detector 104 can be positioned such that it detects little or no backscatter light.

Additionally, the first detector 104 can include other advantageous properties (as described in more detail with respect to FIGS. 3-4) that reduce an amount of incident light 112 absorbed by the first detector 104 during detection. Accordingly, the low quantum efficiency (for example, low light absorption) of first detector 104 indicates that the light 114 transmitted to the tissue site 106 is substantially equal to the incident light 112 from the light source 102. For instance, the majority of light (for example, about 90%, 92%, 94%, 96%, or 98% (+/−1%)) of the incident light 112 can reach the measurement site 106 despite first passing through the first detector 104. In other words, the first detector 104 advantageously absorbs a small percentage of the incident light 112. For example, the first detector 104 can absorb less than 10%, less than 5%, or less than 2% (+/− a few %) of the incident light 112.

By permitting the majority of the light 112 to pass through, the first detector 104 is able to generate a signal corresponds to the intensity of incident light 112 without greatly affecting the intensity of light 114 transmitted to the measurement site 106. Accordingly, the incident light 112 and the light 114 emerging from the first detector 104 have substantially similar intensities. Furthermore, in some cases, the small reduction in light intensity caused by the first detector 104 is negligible because the source power is much higher than after the light has traveled through the measurement site 106.

The second detector 110 can include one or more detectors such as a set of multi-detectors. The second detector 110 is distal the light source 102 and proximal the measurement site 106 with respect to the first detector 104. The second detector 110 is positioned to detect the light 116 (or intensity of light 116) transmitted through the material the light 116 as it emerges from the measurement site 106. After attenuation by the measurement site 106, the second detector 110 detects the attenuated light 116 and outputs a signal responsive to the detected attenuated light 116. In some examples, the second detector 110 includes one or more photodiodes that generate one or more currents proportional to the intensity of the detected light 116.

In some cases where the optical measurement device 100 is a pulse oximetry device attached to a patient's finger, the second detector 110 can be positioned at the patient's fingertip opposite the fingernail so as to detect the light 116 as it emerges from the finger tissue site. The pulse oximetry device can include a clothespin-shaped housing (not shown) having a contoured bed conforming generally to the shape of a finger. For instance, the pulse oximetry device can include an enclosure for receiving a patient's finger. The enclosure can be formed by an upper section pivotably connected with a lower section. The upper section can include the light source 102 and the first detector 104, and the lower section can include the second detector 110. The upper section can be biased with the lower section to close together around a pivot point and thereby sandwiching the measurement site 106 (for example, the finger tissue site).

Figure 1B:
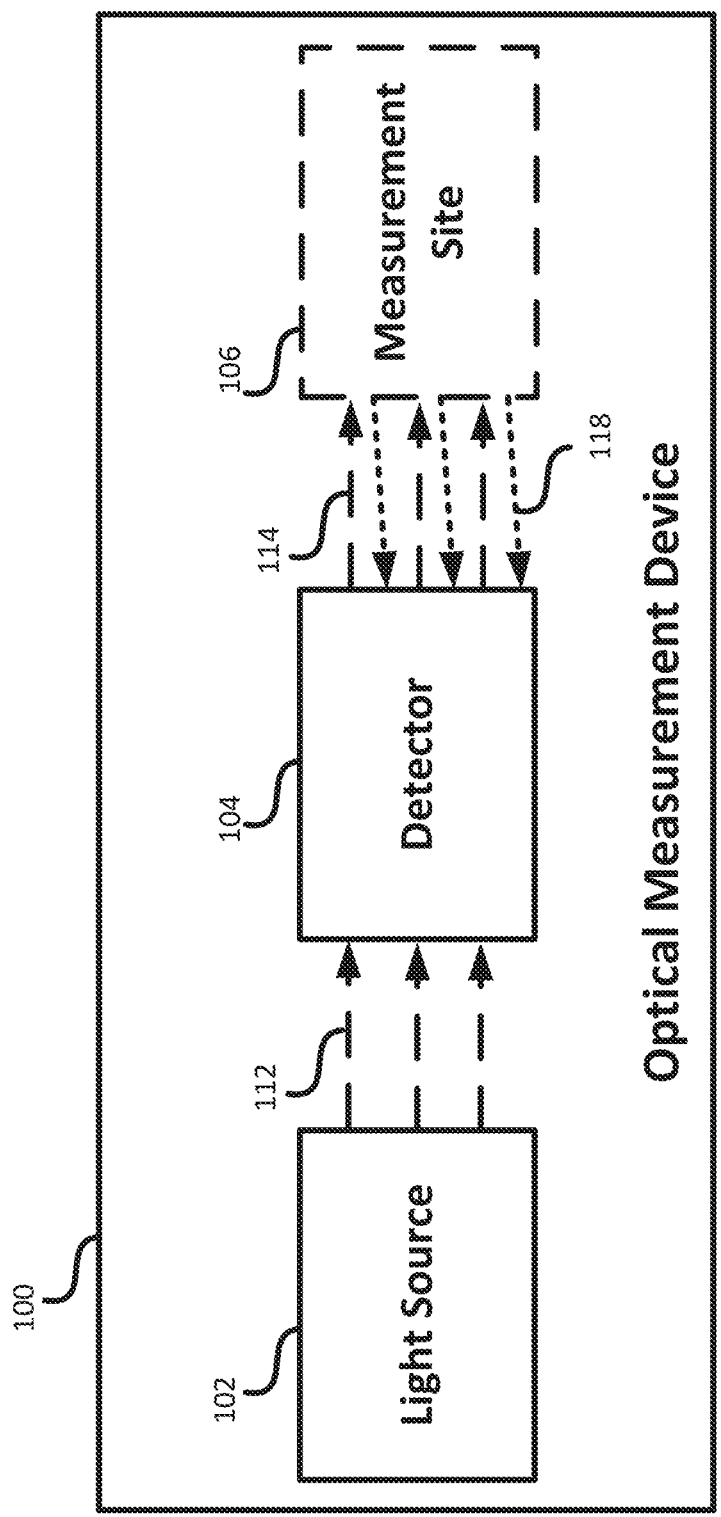

FIG. 1B illustrates block diagram of another example of optical measurement device 100. Similar to FIG. 1A, in this example, the optical measurement device 100 includes a light source 102 and a detector 104. However, in this example, the detector 104 is utilized to detect light transmitted by the light source and/or light reflected or refracted 118 by the measurement site 106. As illustrated, the optical measurement device 100 is configured to be positioned such that the light source 102 is proximal the detector 104 with respect to the tissue site 106.

As described herein, at least a portion of detector 104 can be translucent or partially transparent, thereby acting as a window (and a photodiode) from which all light projected from the light source 102 will pass through prior to reaching the measurement site 106 of the patient. Similarly, the detector 104 can be positioned proximate the measurement site 106 such that it receives light 118 reflected and/or refracted from the measurement site. Thus, the detector 104 can detect a light intensity of the light source 102 and/or light intensity of reflected and/or refracted light 118, and the detector 104 can output one or more signals responsive to the light detections.

Figure 2:
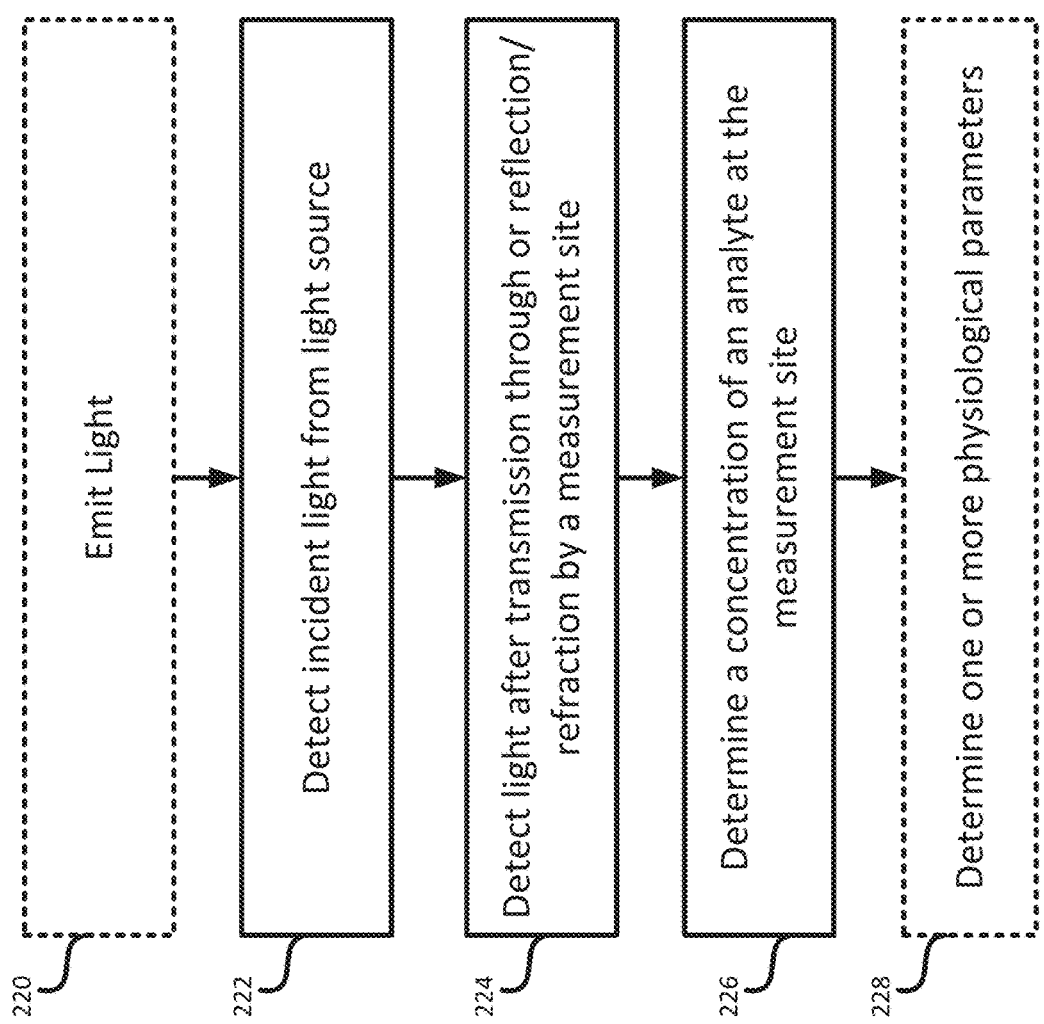
FIG. 2 illustrates a flow diagram of example pulse oximetry device and/or patient monitoring device.

FIG. 2 illustrates an example flow diagram for determining a concentration of an analyte of the measurement site using the optical measurement device 100 of FIG. 1A or 1B. At block 220, the light source 102 transmits, projects, or emits light 112 towards the measurement site 106. As described herein, the measurement site 106 can include one or more various biological or non-biological material. For example, the measurement site can be a tissue site of a patient. Further, as described above with respect to FIG. 1A or 1B, the light source 102 can include one or more LEDs or SLEDs for transmitting optical radiation. In some cases, the light source 102 can emit light having multiple wavelengths such as red, infrared (IR), near IR, or the like.

At block 222, the detector 104 detects incident light 112 emitted by the light source 102. As described above with respect to FIG. 1A or 1B, at least one portion of the detector 104 can be translucent. The detector 104 is positioned proximal to the light source 102 with respect to the measurement site 106, and can act as a window from which all, or substantially all, light projected from the light source 102 will pass through prior to reaching the measurement site 106. Additionally, the detector 104 can advantageously have low quantum efficiency, thereby ensuring the light 114 transmitted to the measurement site 106 has substantially the same intensity as the light projected 112 by the light source 102. The detector 104 can include a photodiode that generates a current proportional to the intensity of the incident light 112. Accordingly, using the detector 104, a system advantageously can accurately determine the real time $I_0$ without substantially reducing the intensity of light transmitted to the measurement site 106.

At block 224, a detector can detect light 116 transmitted through the measurement site, after attenuation by the measurement site 106. In addition or alternatively, a detector can detect light 118 transmitted reflected or refracted from the measurement site 106. For example, as illustrated in FIG. 1A, the detector 110 can detect light 116 as it emerges from the measurement site 106. As another example, as illustrated in FIG. 1B, the detector 104 can detect light 118 as it reflects or refracts from the measurement site 106. The detector 104 or 110 detects the light 116 or 118 and outputs a signal responsive to the detected light 116 or 118. For example, the detector 104, 110 can be a photodiode that generates a current proportional to the intensity of the detected light 116, 118.

At block 226, a concentration of an analyte of interest of the measurement site 106 can be determined (for example, by one or more processors). For example, using the relationship of Equation 2, the concentration can be determined based at least in part on the detected incident light, the detected light transmitted through the measurement site, or the detect light reflected or refracted by the measurement site. Furthermore, in some cases, a transmittance of light, an absorbance of light, and/or a reflectance of light can be determined.

At block 228, the system determine one or more parameters based at least in part on the analyte concentration, transmittance of light, absorbance of light, or reflectance of light determined at block 226. For example, when the optical measurement device is a pulse oximeter or a spectrophotometer, the system can utilize a concentration of an analyte of interest, absorbance, transmittance, reflectance, or other data at a tissue site to determine one or more physiological parameters corresponding to a patient. For example, the system can determine or predict a measurement indicative of a blood constituent of interest, such as glucose, oxygen saturation, methemoglobin, carboxyhemoglobin, glycated hemoglobin, respiration rate, pulse rate, total hemoglobin, other physiological parameters, or other data or combinations of data useful in determining a state or trend of wellness of a patient. An inverse model of the collected data at different blood glucose values can be created and used to predict glucose (or other analyte) values based at least in part on the measured tissue absorbance. Some other examples of parameters that can be used in the development of an inverse model include but are not limited to various measured temperatures (LED, tissue, ambient, photodiode, etc.) and absorbance of various reference materials measured real time.

In some examples, a data collection system (not shown) can be provided which includes a signal processor, a user interface connected to the signal processor, a storage device and a network interface device, which are connected to the signal processor. The data collection system can include a user interface, such as a display. The data collection system can also include optional outputs alone or in combination with the display, such as a storage device and a network interface. The signal processor can include processing logic that determines measurements for desired analytes, such as glucose, based on the signals received from the one or more detectors 104, 110. The signal processor can be implemented using one or more microprocessors or subprocessors (for example, cores), digital signal processors, application specific integrated circuits (ASICs), field programmable gate arrays (FPGAs), combinations of the same, and the like.

Figure 3A:
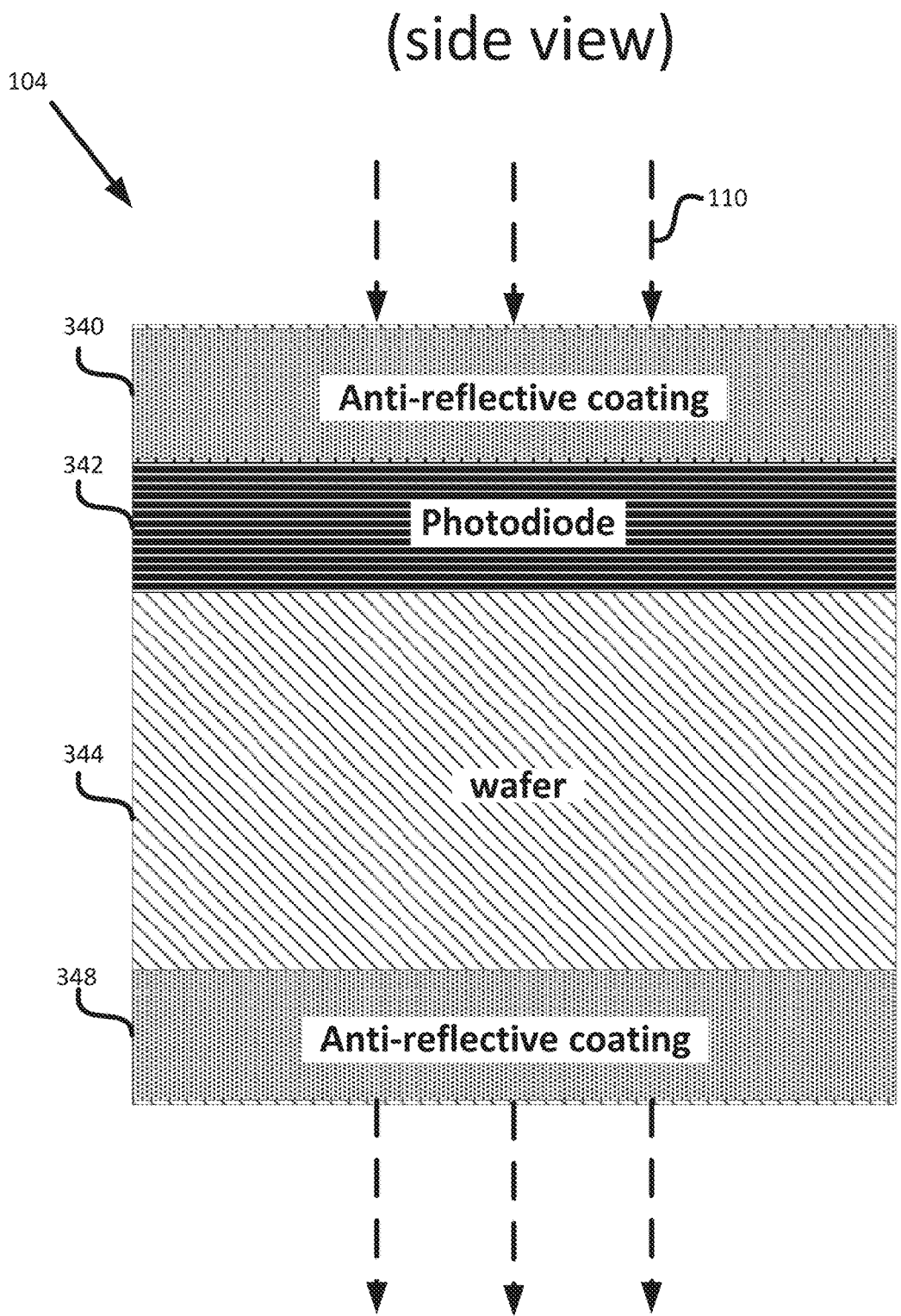
FIG. 3A illustrates a side view of an example detector.

FIG. 3A illustrates a side view of an example detector 104 of the pulse oximetry device 100 of FIG. 1A. In this example, the detector 104 includes four layers. In other examples, the detector 104 can have fewer or more than four layers. The layers can include the same, additional, or equivalent materials to the layers shown in FIG. 3A.

Here, the top layer 340 and the bottom layer 348 include an anti-reflective and/or anti-glare coating. This coating advantageously improves (for example, lowers) the quantum efficiency of the detector 104 (for example, the percentage of light absorbed by the detector 104) by virtually eliminating reflections of the detector 104. As described above with respect to FIG. 1A, it is desirable for the translucent portion of the detector 104 to pass (and not absorb) the light 112 projected from the light source 102. The less light absorbed by the detector 104, the more accurate the light intensity detected by the detector 104.

The second layer 342 includes a photodiode that converts the light 112 into current. In some examples, at least a portion of the second or photodiode layer 342 can be translucent. The photodiode layer 342 can have varying thicknesses across multiple embodiments. For example, the photodiode layer 342 can be as thick as 1, 2, 3, 4, 5, 6, 7, 8, 9, 10, 11, 12, 13, 14, or 15 nanometers (+/− a few nanometers) or can be as thick as a few micrometers. As mentioned below with respect to FIG. 4, the thickness of the photodiode layer 344 can affect the quantum efficiency or light absorption of the detector 104. Thus, in some examples, the photodiode layer 342 can advantageously be thin to provide improved (for example lowered) quantum efficiency. The photodiode layer 342 can include a combination of one or more of an Indium-Gallium-Arsenide (InGaAs) PIN photodiode or a silicon (Si) PIN photodiode. For example, the photodiode 342 may include a layer of Silicon PIN photodiode and an over-layer of Indium-Gallium-Arsenide (InGaAs) PIN photodiode.

The third layer 344 includes a wafer or thin slice of semiconductor material. In some examples, the third layer 344 includes an N-type Indium Phosphide (N—InP) wafer. The third layer 344 can have one of a plurality of thicknesses. For instance, the third layer 344 can be 1, 2, 3, 4, 5, 6, 7, 8, 9, 10, 11, 12, 13, 14, or 15, 20, 50, 100 micrometers thick (+/− a few micrometers).

Figure 3B:
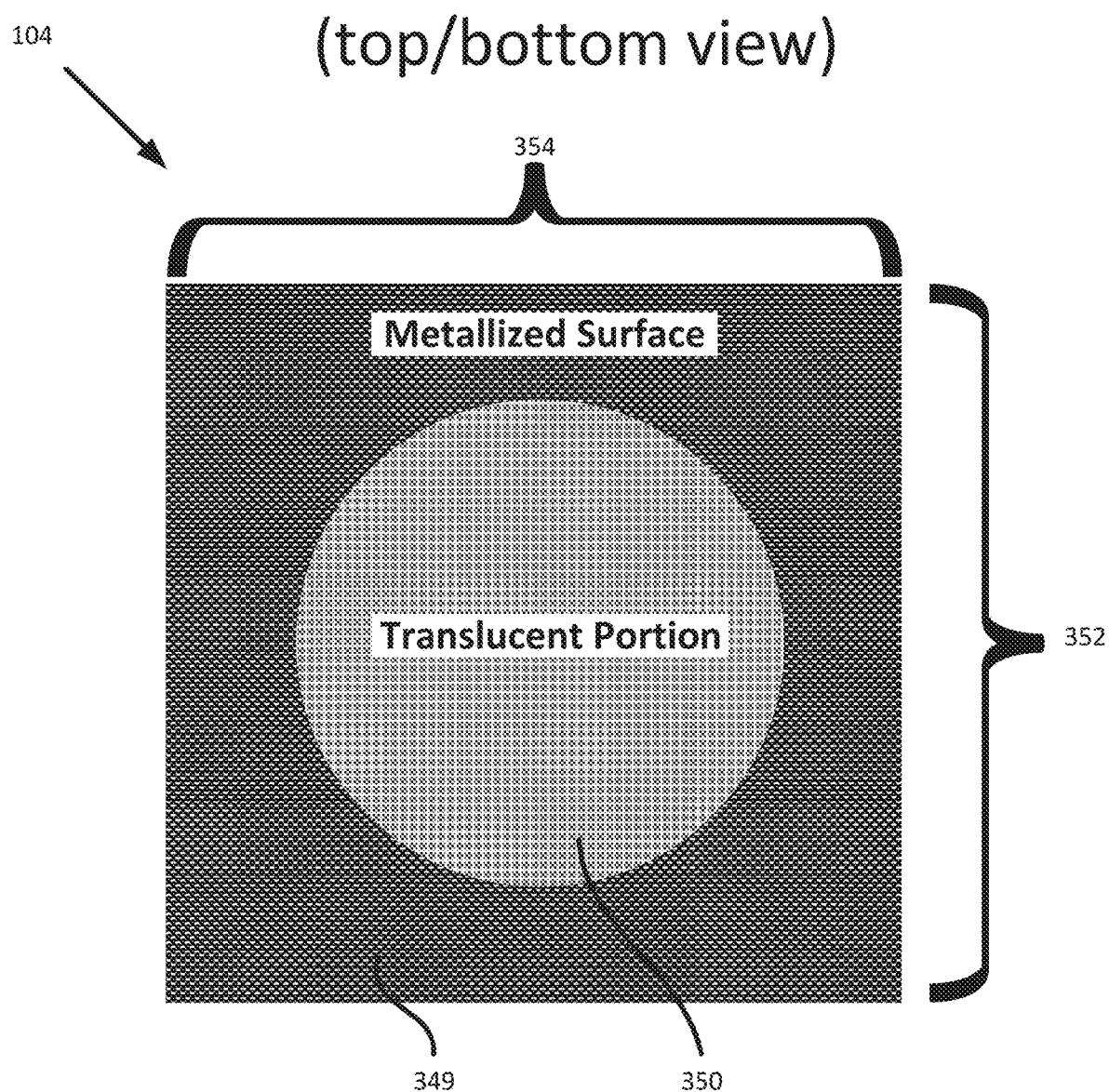
FIG. 3B illustrates a top/bottom view of an example detector.

FIG. 3B illustrates a top/bottom view of an example detector. Here, the detector 104 has a translucent portion 350 and an opaque portion 349. In some examples, the detector 104 can be fully or mostly translucent. While the translucent portion 350 is depicted as having a circular shape, the translucent portion 350 can take any shape. The detector 104 can include more than one translucent portion.

The opaque portion 349 can include a metalized surface. For example, the opaque portion 349 can include a metalized surface for anode/cathode bond pads. As mentioned above, the with respect to FIG. 3A, the surface of the detector 104 can have an antireflective coating to improve quantum efficiency.

In some examples, the translucent portion can be generally circular and have a diameter of approximately 2, 4, 5, 6, 7, 8 mm (+/− a few millimeters). In some examples the area of the translucent portion can be approximately 5, 6, 7, 10, 20, 40 or 80 square millimeters (+/− a few square millimeters).

The detector 104 can take the shape of a rectangular prism, cube, cylinder, or any other shape. In some examples, the width 354 and/or length 352 of the detector 104 is approximately 3 millimeters. In other examples, the width 354 and/or length 352 can be in the range of 1 to 10 millimeters (+/− a few millimeters).

Figure 4:
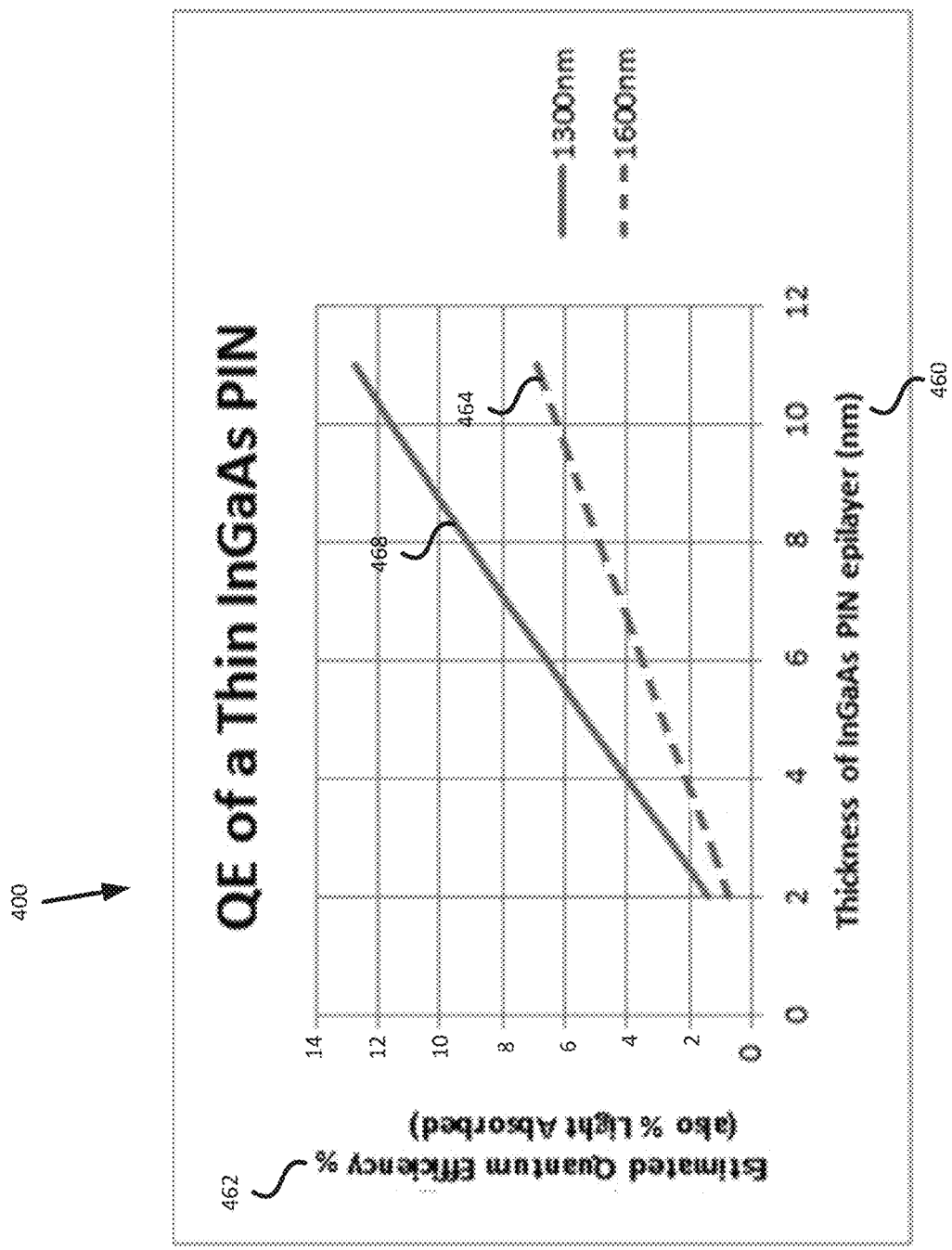
FIG. 4 illustrates examples of light absorption data collected by a detector having varying thickness.

FIG. 4 illustrates examples of quantum efficiency data of a plurality of detectors 104 having photodiode layers of varying thicknesses. As described above, the projected light 112 from the light source 102 is transmitted through a photodiode layer 342 of the detector 104 prior to reaching the tissue site 106 of the patient. FIG. 4 illustrates how the thickness of the photodiode layer 342 (in this example an InGaAs PIN epilayer) affects the quantum efficiency (and total light absorbed) of the detector 104.

In FIG. 4, the X axis 460 of the line chart 400 indicates the thickness (in nanometers) of the InGaAs PIN epilayer of the detector 104. The Y axis 462 of the line chart 400 indicates the estimated quantum efficiency (also light absorbed) expressed as a percentage. The "quantum efficiency" is the ratio of light absorbed to light received (for example, light projected by the light source). Thus, if all photons of a certain wavelength are absorbed, then the quantum efficiency at that particular wavelength is unity. In other words, low light absorption corresponds to low quantum efficiency.

Line 464 represents data values for projected light with wavelength of 1600 nanometers and line 468 represents data values for projected light with wavelength of 1300 nanometers. As indicated by the positive slopes of the lines 464 and 468, as the thickness of the photodiode layer increases, the total light absorbed by the detector increases. Accordingly, in some examples, the detector 104 can have a thin photodiode layer (for instance, 2 or 3 nm) to advantageously reduce the amount of light absorbed by the detector 104, thereby providing the tissue site 106 with light having intensity similar to that of the light as it emerges from the light source 102.

In addition, lines 464 and 468 of FIG. 4 indicate that as the wavelength of projected light increases, the quantum efficiency decreases. Accordingly, in some examples, the light source emits light with longer wavelength (for instance, approximately 1600 nanometers) to advantageously reduce the amount of light absorbed by the detector 104.

Embodiments have been described in connection with the accompanying drawings. However, it should be understood that the figures may not be drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, methods, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. An optical measurement device comprising:
   a light source configured to emit light to a measurement site;
   a first detector positioned within an optical path between the light source and the measurement site, wherein at least a portion of the light emitted by the light source passes through the first detector prior to reaching the measurement site; and
   a second detector configured to receive the at least a portion of the light after attenuation by the measurement site.

2. The device of claim 1, wherein the light source comprises one or more light emitting diodes, and wherein the measurement site comprises non-biological material.

3. The device of claim 1, wherein the light source comprises one or more superluminescent light emitting diodes, and wherein the measurement site comprises biological material.

4. The device of claim 1, wherein the second detector is configured to be positioned opposite the first detector with respect to the measurement site.

5. The device of claim 1, further comprising:
   a housing configured to house the light source; and
   flexible connections or flexible cabling configured to electrically connect the first detector to the housing.

6. The device of claim 1, wherein the first detector comprises an antireflective (AR) coating layer, a photodiode layer, and a wafer layer.

7. The device of claim 1, wherein the first detector comprises an at least partially transparent portion, wherein the at least a portion of light emitted by the light source passes through the at least partially transparent portion.

8. The device of claim 1, wherein the first detector is configured to output a first signal responsive to first light sensed by the first detector, wherein the second detector is configured to output a second signal responsive to second light sensed by the second detector, and wherein a processor receiving the first signal and the second signal or data responsive to the signals is configured to determine one or more physiological parameters of the patient.

9. The device of claim 8, wherein the one or more physiological parameters comprises at least one of oxygen saturation, respiration rate, or pulse rate.

10. The device of claim 8, wherein the one or more physiological parameters corresponds to at least one of glucose, methemoglobin, carboxyhemoglobin, glycated hemoglobin, total hemoglobin.

11. A method of determining one or more physiological parameters, the method comprising:
    controlling a light source to emit light towards a measurement site, wherein at least a portion of the light passes through a first detector before reaching the measurement site, and wherein the at least a portion of the light is received by a second detector after attenuation by the measurement site;
    receiving a first signal output by the first detector responsive to first light sensed by the first detector;
    receiving a second signal output by the second detector responsive to second light sensed by the second detector; and
    determining one or more physiological parameters based at least in part on the first signal and the second signal.

12. The method of claim 11, wherein the one or more physiological parameters comprises blood glucose concentration.

13. The method of claim 11, wherein the measurement site comprises non-biological material.

14. An optical measurement device comprising:
    a light source configured to emit light toward a measurement site; and
    a detector positioned within an optical path between the light source and the measurement site, wherein the detector is configured to sense a first portion of the light before the first portion of the light reaches the measurement site, and wherein a second portion of the light passes through the detector before the second portion of the light reaches the measurement site.

15. The device of claim 14, wherein the detector is further configured to detect the second portion of the light after the second portion of the light interacts with the measurement site.

16. The device of claim 15, wherein the detector is configured to output a first signal responsive to the first portion of the light and output a second signal responsive to the second portion of the light, and wherein an oximeter receives the first signal and the second signal and determines one or more physiological parameters of the patient based at least in part on the first signal and the second signal.

17. The device of claim 14, wherein the detector is a first detector, wherein the device further comprises a second detector configured to receive the second portion of the light after the second portion of the light is attenuated by the measurement site.

18. The device of claim 17, wherein the first detector is configured to output a first signal responsive to the first portion of the light, wherein the second detector is configured to output a second signal responsive to the second portion of the light, and wherein an oximeter receives the first signal and the second signal and determines one or more physiological parameters of the patient based at least in part on the first signal and the second signal.

19. The device of claim 14, wherein the light source comprises one or more superluminescent light emitting diodes, and wherein the measurement site comprises non-biological material.

20. The device of claim 14, wherein the light source comprises one or more light emitting diodes, and wherein the measurement site comprises biological material.

* * * * *